United States Patent [19]

Hiramatsu et al.

[11] Patent Number: 4,812,163
[45] Date of Patent: Mar. 14, 1989

[54] PHENOXYACETIC ACIDS AND HERBICIDES COMPRISING THEM AS ACTIVE INGREDIENTS

[75] Inventors: Toshiyuki Hiramatsu; Shizuo Azuma; Koji Nakagawa, all of Iwakuni; Yataro Ichikawa, Tokorozawa, all of Japan

[73] Assignee: Teijin, Limited, Osaka, Japan

[21] Appl. No.: 172,988

[22] Filed: Mar. 18, 1988

Related U.S. Application Data

[63] Continuation of Ser. No. 849,677, Apr. 9, 1986, abandoned.

[30] Foreign Application Priority Data

Feb. 14, 1986 [JP] Japan .................................. 61-29039

[51] Int. Cl.$^4$ .................. C07D 241/44; C07D 403/12; C07D 207/08; A01N 43/60
[52] U.S. Cl. ........................................ 71/92; 544/354; 548/540; 560/41; 560/72
[58] Field of Search ............................ 544/354; 71/92

[56] References Cited

U.S. PATENT DOCUMENTS 3,439,018 4/1969 Brookes et al. .................... 544/164
4,629,493 12/1986 Ura et al. .............................. 71/92

FOREIGN PATENT DOCUMENTS 23785  2/1981  European Pat. Off. .
42750 12/1981  European Pat. Off. ............ 544/354
46468  3/1982  European Pat. Off. .
57-35575 2/1982 Japan ................................. 544/354

OTHER PUBLICATIONS

"Phenoxyalkane-and Phenoxyalkene Carboxylic Acid, Their Derivatives and Their Use".
Bauer et al., Chem. Abstracts 96: 7068u (1981).

Primary Examiner—Mark L. Berch
Assistant Examiner—E. Bernhardt
Attorney, Agent, or Firm—Wenderoth, Lind & Ponack

[57] ABSTRACT

A phenoxyacetic acid represented by the following formula (I)

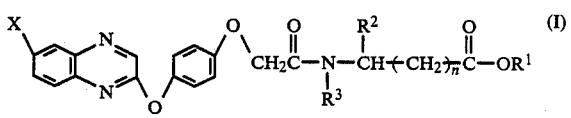

wherein X represents a halogen atom or $CF_3$, $R^1$ and $R^3$ are identical or different and each represents a hydrogen atom or an alkyl group having not more than 5 carbon atoms, $R^2$ represents a hydrogen atom, a lower alkyl group, a phenyl group, a benzyl group, $-CH_2CH_2SCH_3$, $-CH_2OH$, $-CH(CH_3)OH$, $-CH_2SH$, $-CH_2COOCH_3$,

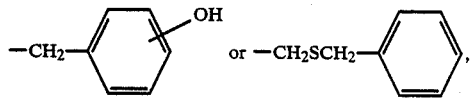

or $R^2$ and $R^3$ together may form $-CH_2CH_2CH_2-$ or $-CH_2CH_2CH(OH)-$, and n is 0, 1 or 2, or a salt at the carboxyl group of the phenoxyacetic acid of the above formula in which $R^1$ is a hydrogen atom. The compound is useful, as a herbicide, for eradicating weeds, especially narrow-leaved weeds.

11 Claims, No Drawings

PHENOXYACETIC ACIDS AND HERBICIDES COMPRISING THEM AS ACTIVE INGREDIENTS

This application is a continuation of now abandoned application Ser. No. 849,677, filed Apr. 9, 1986.

This invention relates to a phenoxyacetic acid and a herbicide comprising it as an active ingredient. More specifically, it relates to a phenoxyacetic acid having selective herbicidal activity which kills narrow-leaved weeds without substantially killing broad-leaved plants and without killing narrow-leaved crop plants, and a herbicide comprising it as an active ingredient.

Herbicides of the type which selectively kills broad-leaved weeds, typified by 2,4-dichlorophenoxyacetic acid, are known as selective herbicidally active compounds. The selectivity of the herbicidal activity of 2,4-dichlorophenoxyacetic acid is between narrow-leaved plants including crop plants and weeds and broad-leaved plants including crop plants and weeds. It is known that 2,4-dichlorophenoxyacetic acid has very little or no activity against narrow-leaved plants [see, for example, Nature, Vol. 155, page 498 (1945)]. It is known on the other hand that compounds resulting from introduction of a chloro- or trifluoromethyl-substituted phenoxy group or a chloro- or trifluoromethyl-substituted pyridyloxy group into the aromatic group of the above compound have the activity of selectively killing narrow-leaved plants (see Japanese Laid-Open Patent Publications Nos. 44631/1976, 125626/1977, 15825/1977 and 2438/1978, and Japanese Patent Publication No. 8727/1979). However, these compounds also kill useful narrow-leaved crops such as rice or corn.

Japanese Laid-Open Patent Publication No. 35575/1982 describes quinoxaline derivatives of the following formula

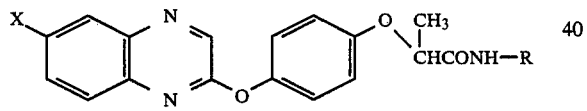

wherein X is a halogen atom or trifluoromethyl, R is $-CH_2COOR^1$, $-R^2-O-R^3$ or

$R^1$, $R^2$ and each $R^4$ represents a lower alkyl group, and $R^3$ is a hydrogen atom or a lower alkyl group.

The patent document discloses that these quinoxaline derivatives show excellent herbicidal activity particularly against gramineous plants.

European Laid-Open Patent Publication No. 0046468 discloses that a compound of the following formula

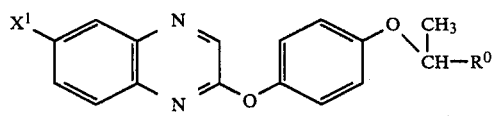

wherein $X^1$ is $-CF_3$ or $-CH_3$, $R^0$ is, for example, $-COR^{01}$, $R^{01}$ is, for example,

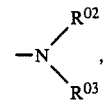

and $R^{02}$ and $R^{03}$ are H, lower alkyl, phenyl or $-CH_2COOC_2H_5$, is used as a herbicide which is particularly effective for controlling gramineous weeds without phytotoxicity to broad-leaf crop plants or broad-leaf weeds, especially in a post-emergence treatment.

European Laid-Open Patent Publication No. 0046467 describes that a compound of the following formula

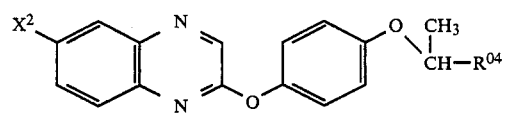

wherein $X^2$ is halogen, $R^{04}$ is, for example, $-COR^{05}$, $R^{05}$ is, for example, $-NHR^{06}$, and $R^{06}$ is $C_1-C_4$alkoxycarbonylalkyl, hydroxyalkyl, phenyl, $C_1-C_4$alkoxyalkyl, or di($C_1-C_4$)alkylamino, has the same herbicidal activity as the compound disclosed in European Laid-Open Patent Publication No. 0046468.

European Laid-Open Patent Publication No. 0047972 describes that a compound of the following formula

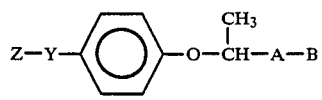

wherein Z is

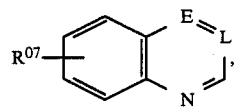

Y is, for example, $-O-$, A is, for example, a direct bond, B is, for example,

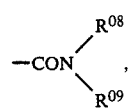

$R^{08}$ is H or $C_1-C_4$ alkyl, $R^{09}$ is H, $C_1-C_{10}$ alkyl, phenyl (which may be mono- or di-dibstituted by Cl and/or $CH_3$) or $-CH(Q)COOR$ (Q is H or $CH_3$), E is CH, N or

and L is CH or N, increases the carbohydrate content of plants.

Agricultural and Food Chemistry, vol. 4, page 690 (1956) describes the biological activities of amides of 2,4-dichlorophenoxy-2-propionic acid with alanine, aspartic acid, leucine, methionine, phenylalanine and threonine when they are applied to foliage of useful crops such as corn, barley, cucumber, sunflower and soybean. Specifically, it states that the amides of alanine, leucine and threonine almost completely killed broad-leaved crops such as soybean, sunflower and cucumber and slightly inhibited growth of narrow-leaved corn such as barley and corn, whereas the amides of aspartic acid, methionine and phenylalanine showed little or no effect against broad-leaved and narrow-leaved crops.

It is an object of this invention therefore to provide a novel phenoxyacetic acid.

Another object of this invention is to provide a selective herbicide having selective herbicidal activity.

Another object of this invention is to provide a selective herbicide which selectively kills narrow-leaved weeds without substantially inhibiting the growth of broad-leaved plants and substantially affecting useful narrow-leaved plants.

Another object of this invention is to provide a selective herbicide which kills many narrow-leaved plants or inhibits their growth without causing substantial phytotoxicity to narrow-leaved crops such as rice, corn and wheat and various broad-leaved crops such as soybean, cotton, beet and sunflower, and therefore when applied to a locus where the aforesaid useful crops and hazardous weed grow together, can create a condition in which the useful crops easily grow beyond the growth of the weeds.

Another object of this invention is to provide a selective herbicide applicable by foliar spraying and soil treatment, which can kill, or inhibit the growth of, weeds by application to their foliage, and also can inhibit the emergence of weeds without substantially inhibiting the emergence of useful crops by application to the soil before emergence.

Another object of this invention is to provide a selective herbicide which has a low toxicity to animals and fish and remains in the soil only in little amounts.

Another object of this invention is to provide a method of eradicating weeds by using the aforesaid compounds of herbicides of this invention.

Further objects of this invention along with its advantages will become apparent from the following description.

These objects and advantages of this invention are achieved by a phenoxyacetic acid represented by the following formula (I)

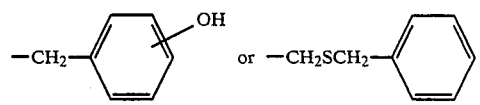

wherein X represents a halogen atom or CF₃, R¹ and R³ are identical or different and each represents a hydrogen atom or an alkyl group having not more than 5 carbon atoms, R² represents a hydrogen atom, a lower alkyl group, a phenyl group, a benzyl group, —CH₂CH₂SCH₃, —CH₂OH, —CH(CH₃)OH, —CH₂SH, —CH₂COOCH₃,

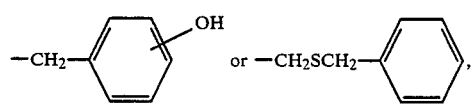

or R² and R³ together may form —CH₂CH₂CH₂— or —CH₂CH₂CH(OH)—, and n is 0, 1 or 2, or a salt at the carboxyl group of the phenoxyacetic acid of the above formula in which R¹ is a hydrogen atom.

In the formula (I), X is a halogen atom or CF₃. Fluorine, chlorine and bromine are preferred as the halogen atom.

R¹ and R³ are identical or different and each represent a hydrogen atom or an alkyl group having not more than 5 carbon atoms. The alkyl group having not more than 5 carbon atoms may be linear or branched, and includes, for example, methyl, ethyl, n-propyl, iso-propyl, n-butyl iso-butyl, sec-butyl, t-butyl and n-pentyl.

R² is a hydrogen atom, a lower alkyl group, a phenyl group, a benzyl group, —CH₂CH₂SCH₃, —CH₂OH, —CH(CH₃)OH, —CH₂SH, —CH₂COOCH₃,

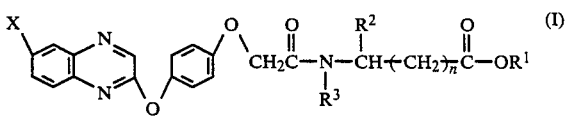

The lower alkyl may be linear or branched, and preferably has 1 to 5 carbon atoms. Specific examples of the alkyl group are the same as given above for R¹ and R³.

R² and R³ together may form —CH₂CH₂CH₂— or —CH₂CH₂ CH(OH)—.

n is 0, 1 or 2.

In formula (I), X is preferably a halogen atom, especially preferably a chlorine atom, R¹ is preferably a hydrogen atom or an alkyl group having 1 to 4 carbon atoms. R² is especially preferably a hydrogen atom, an alkyl group having 1 to 4 carbon atoms, a phenyl group, a benzyl group, or —CH₂CH₂SCH₃. Preferably, R³ is a hydrogen atom, methyl, or ethyl, or together with R², forms —CH₂CH₂CH₂—. Especially preferably, R³ is a hydrogen atom.

Preferably, the compounds of formula (I) are phenoxyacetic acids of the following formula (I)-a

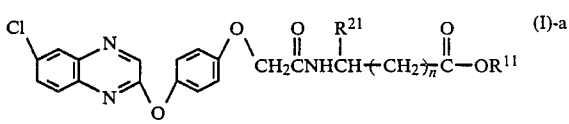

wherein R¹¹ represents a hydrogen atom or an alkyl group having not more than 4 carbon atoms, R²¹ represents a hydrogen atom, an alkyl group having not more than 4 carbon atoms, a phenyl group or a benzyl group, and n is as defined above, and salts at the carboxyl group of compounds of the above formula in which R¹¹ is a hydrogen atom.

Especially preferred among the compounds of formula (I) or (I)-a are phenoxyacetic acids represented by the following formula

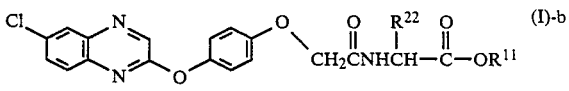

wherein R¹¹ is as defined above, and R²² is a phenyl or benzyl group, and salts of compounds of formula (I)-b in which R¹¹ is a hydrogen atom.

Specific examples of the compounds of formula (I) [including formulae (I)-a and (I)-b throughout the specification] are given below.

(100) N-[4-(6-chloro-2-quinoxalyloxy)phenoxy]acetylglycine ethyl ester, (102) N-[4-(6-chloro-2-quinoxalyloxy)phenoxy]acetylalanine methyl ester,
(104) N-[4-(6-chloro-2-quinoxalyloxy)phenoxy]acetylphenylalanine methyl ester,
(106) N-[4-(6-chloro-2-quinoxalyloxy)phenoxy]acetylphenylglycine methyl ester,
(108) N-[4-(6-chloro-2-quinoxalyloxy)phenoxy]acetylphenylglycine n-butyl ester,
(110) N-[4-(6-chloro-2-quinoxalyloxy)phenoxy]acetylaspartic acid dimethyl ester,
(112) N-[4-(6-chloro-2-quinoxalyloxy)phenoxy]acetylleucine methyl ester,
(114) N-[4-(6-chloro-2-quinoxalyloxy)phenoxy]acetyl-2-amino butyric acid methyl ester,
(116) N-[4-(6-chloro-2-quinoxalyloxy)phenoxy]acetyl-N-methylene methyl ester,
(118) N-[4-(6-chloro-2-quinoxalyloxy)phenoxy]acetylphenylglycine,
(120) N-[4-(6-chloro-2-quinoxalyloxy)phenoxy]acetylphenylglycine mono-ethylammonium salt,
(122) N-[4-(6-chloro-2-quinoxalyloxy)phenoxy]acetylphenylglycine sodium salt,
(124) N-[4-(6-chloro-2-quinoxalyloxy)phenoxy]acetyl-3-amino propionic acid methyl ester,
(126) N-[4-(6-chloro-2-quinoxalyloxy)phenoxy]acetyl-4-amino butyric acid methyl ester,
(128) N-[4-(6-chloro-2-quinoxalyloxy)phenoxy]acetylproline methyl ester,
(130) N-[4-(6-chloro-2-quinoxalyloxy)phenoxy]acetylmethionine methyl ester,
(132) N-[4-(6-chloro-2-quinoxalyloxy)phenoxy]acetylglycine n-butyl ester,
(134) N-[4-(6-fluoro-2-quinoxalyloxy)phenoxy]acetylglycine ethyl ester,
(136) N-[4-(6-bromo-2-quinoxalyloxy)phenoxy]acetylglycine methyl ester,
(138) N-[4-(6-trifluoromethyl-2-quinoxalyloxy)phenoxy]acetyl-glycine ethyl ester, It is seen from the structure shown in formula (I) that the compound of formula (I) is composed of the phenoxyacetic acid skeletal portion on the left side and the aminocarboxylic acid skeletal portion on the right side. The aminocarboxylic acid forming the aminocarboxylic acid skeletal portion of the compound of formula (I) may be any of alpha-, beta- and gamma-aminocarboxylic acids as can be seen from the above specific examples. For example, it includes alpha-amino acids such as glycine, alanine, valine, isoleucine, leucine, cysteine, methionine, phenylalanine, phenylglycine, serine, threonine and proline; beta-amino acids such as beta-aminopropionic acid, beta-aminobutyric acid, beta-aminopentanoic acid, beta-aminohexanoic acid, and beta-amino-gamma-methylpentanoic acid; gamma-amino acids such as gamma-aminobutyric acid, gamma-aminopentanoic acid, gamma-aminohexanoic acid, gamma-aminoheptanoic acid, gamma-amino-delta-methylhexanoic acid.

The compounds of formula (I) may be produced, for example, by processes 1 to 3 shown by the following reaction schemes.

Process 1

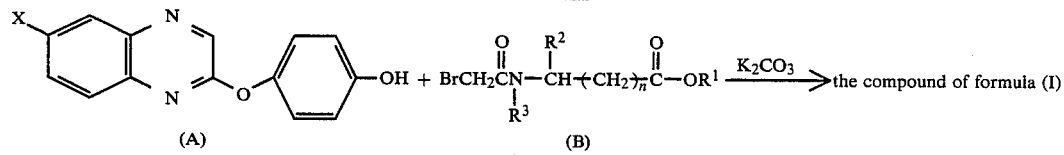

(A)    (B)

Process 2

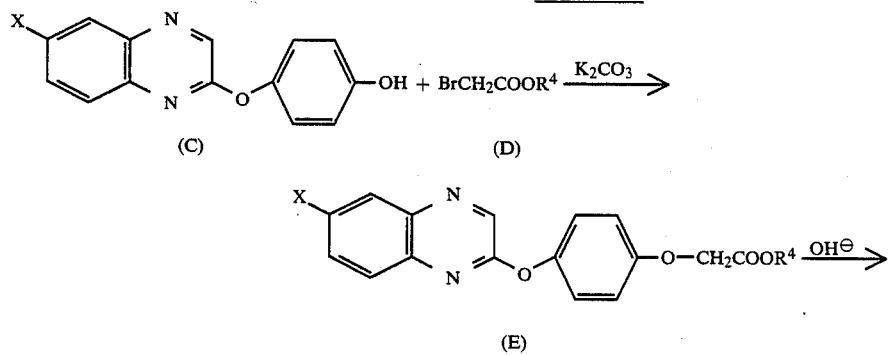

(C)    (D)

(E)

(F)

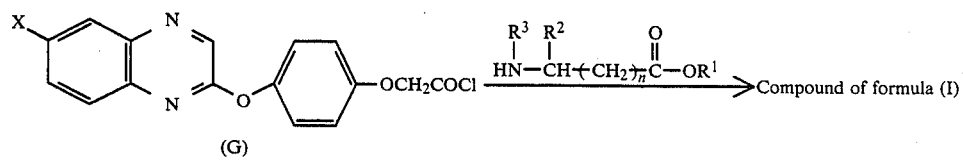

(G)

-continued
Process 3

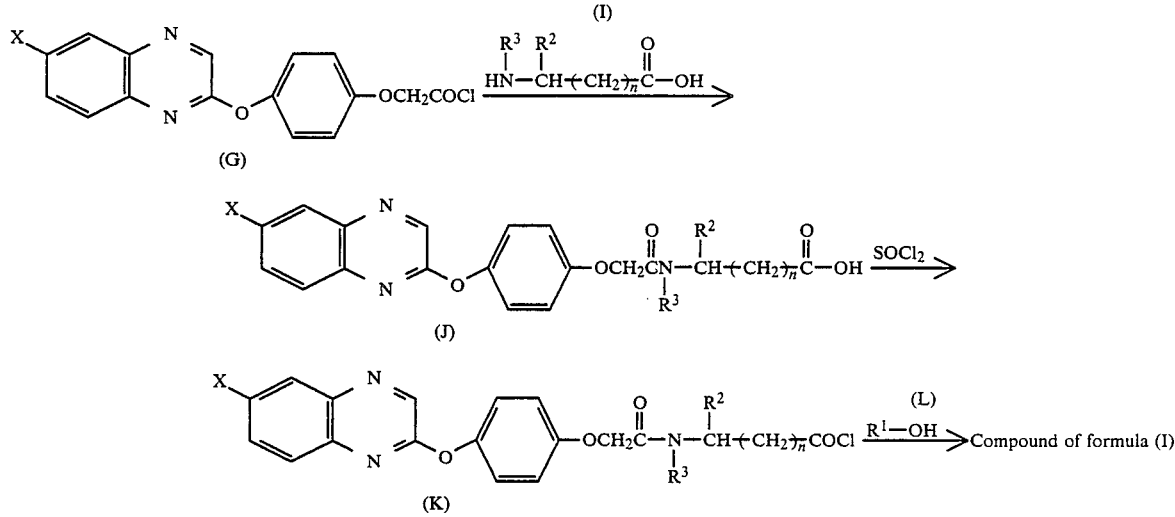

In the above reaction schemes, X in compounds (A), (C), (E), (F), (G), (J) and (K) is as defined hereinabove. $R^2$ and $R^3$ in formulae (B), (H), (J) and (K) and $R^1$ in formulae (B), (H) and (L) are as defined above. $R^4$ in formulae (D) and (E) is a lower alkyl group, for example, a linear or branched alkyl group having 1 to 4 carbon atoms.

Processes 1 to 3 can be carried out by methods known per se.

A compound of formula (I) in which $R^1$ is a hydrogen atom can be produced by process 1 or 2 by using a compound of formula (B) or (H) in which $R^1$ is a hydrogen atom; or by using a compound of formula (B) or (H) in which $R^1$ is an alkyl group having not more than 5 carbon atoms, and producing a compound of formula (I) in which $R^1$ is the corresponding alkyl group, and thereafter hydrolyzing this compound.

The salt at the carboxyl group of a compound of formula (I) in which $R^1$ is a hydrogen atom can be produced by reacting the corresponding carboxylic acid with a basic compound, for example, an alkali metal hydroxide, an alkaline earth metal hydroxide, ammonia, or an amine.

According to this invention, there are also provided phenoxypropionic acids represented by the following formula (II)

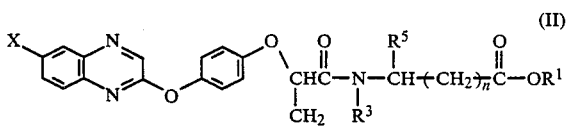

wherein X, $R^1$, $R^3$ and n are as defined above, $R^5$ a phenyl group, a benzyl group, —CH$_2$CH$_2$SCH$_3$, —CH$_2$OH, —CH(CH$_3$)OH, —CH$_2$SH, —CH$_2$COOCH$_3$,

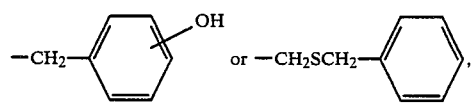

or $R^5$ and $R^3$ together may form —CH$_2$CH$_2$CH$_2$— or —CH$_2$CH$_2$CH(OH)—, and salts at the carboxyl group of compounds of formula (II) in which $R^1$ is a hydrogen atom, as analogous compounds in addition to the phenoxyacetic acids of formula (I) and their salts.

The compound of formula (II) can be produced by the same processes as in the production of the compounds of formula (I).

Examples of the compounds of formula (II) and their salts are shown below.

(200) N-2-[4-(6-chloro-2-quinoxalyloxy)phenoxy]propionyl-phenylglycine methyl ester
(202) N-2-[4-(6-chloro-2-quinoxalyloxy)phenoxy]propionyl-phenylglycine
(204) N-2-[4-(6-chloro-2-quinoxalyloxy)phenoxy]propionyl-phenylglycine monoethylammonium salt
(206) N-2-[4-(6-chloro-2-quinoxalyloxy)phenoxy]propionyl-phenylglycine sodium salt
(208) N-2-[4-(6-chloro-2-quinoxalyloxy)phenoxy]propionyl-leucine methyl ester
(210) N-2-[4-(6-chloro-2-quinoxalyloxy)phenoxy]propionyl-aspartic acid methyl ester
(212) N-2-[4-(6-chloro-2-quinoxalyloxy)phenoxy]propionyl-methionine methyl ester
(214) N-2-[4-(6-chloro-2-quinoxalyloxy)phenoxy]propionyl-3-amino propionic acid methyl ester
(216) N-2-[4-(6-chloro-2-quinoxalyloxy)phenoxy]propionyl-4-amino butyric acid methyl ester The compounds of formula (I) [including formulae (I)-a and (I)-b] and formula (II) and their salts have the property of affecting the metabolism of plants to inhibit the growth of a certain kind of plants, regulate the growth of a certain kind of plants, dwarf a certain kind of plants, or to kill a certain kind of plants.

The compounds of formulae (I) and (II) and their salts provided by this invention show selective herbicidal activity, and particularly have the marked property of selectively killing narrow-leaved weeds without substantially inhibiting the growth of broad-leaved plants and substantially affecting narrow-leaved useful plants.

Accordingly, the present invention also provides a herbicide comprising the phenoxyacetic acid of formula (I) or its salt at the carboxyl group when $R^1$ is a hydrogen atom as a herbicidally active ingredient.

The compounds of formula (I) provided by this invention can also be applied to seeds of plants, and to plants in various growth stages through foliage or roots. In other words, the compounds of this invention, either as such or as a composition, are applied to plants whose growth is to be inhibited, namely plants whose metabolism is to be regulated, seeds of such plants, a locus where such plants are growing, or a locus where the growth of such plants is anticipated, in amounts sufficient to regulate the metabolism of the plants.

The metabolism of plants can be regulated by applying the compounds of this invention at a rate of 1 g to 2 kg, preferably 5 g to 1 kg, especially preferably 10 g to 200 g, per 10 acres.

When it is desired to inhibit the growth of, or eradicate, hazardous plants by the compounds of this invention, the compounds, either as such or as a composition, can be applied directly to the plants or their seeds or to the soil in amounts sufficient to inhibit the growth of, or eradicate, the plants in a locus where beneficial plants or their seeds and the hazardous plants or their seeds are growing together or are likely to grow together.

The hazardous plants may be defined as plants which come into an environment created by man, such as a paddy or an upland farm, from the surrounding area, and grow there and which are considered by man to be useless in that environment or do harm to it. Such hazardous plants are generally called weeds. Examples of the weeds to which the compounds of this invention are to be applied are shown below.

*Sorghum halepense,*
*Digitaria adscendens,*
*Setaria faberi,*
*Panicum texanum,*
*Echinochloa crus-galli,*
*Setaria viridis,*
*Poa annua,*
*Axonopus affinis,*
*Bachiaria platyphylla,*
*Bromus tectorum,*
*Cynodon dactylon,*
*Panicum dichotomiflorum,*
*Paspalum dilatatum*
*Echinochloa colona,*
*Panicum capillare,* and
*Setaria lutescens.*

The beneficial plants in the above case are, for example, plants producing cereals, and lawns. Since the compounds of this invention exert little or no adverse effect on the growth of not only varous broad-leaved plants such as soybean, cotton, sunflower and beet but also narrow-leaved crops such as rice, corn and wheat, they are very suitable for application to paddies and upland farms for cultivating these plants. By applying the compounds of this invention to a locus where lawns are growing, the emergence and growth of weeds can be inhibited.

In some cases, it is desirable to apply the compounds of this invention while hazardous plants do not grow so much, particularly while the height of the hazardous plants is lower, or a little bit higher, than the height of beneficial plants.

When weeds are to be eradicated by using the compounds of this invention, the compounds can be applied either as such or as a composition to weeds to be eradicated, their seeds, or a locus where such weeds are growing, or are likely to grow, for example in a crop cultivating area, in amounts sufficient for eradication.

The herbicide of this invention shows a very good effect against narrow-leaved weeds. When used in dosages which exhibit this effect, the herbicide does not substantially injure the aforesaid useful crops.

The compounds of formula (I)-a are especially advantageously used to eradicate weeds in such crops as, for example, broad-leaved crops such as soybean, cotton, sunflower or beet. The compounds of formula (I)-b are particularly advantageously used to kill weeds in such a cultivating area where the useful plants are rice or corn.

The compounds of this invention can be used in usual formations such as a solution, an emulsifiable concentrate, a suspension, a dust, a paste or granules.

Such formulations are prepared by using at least one agriculturally acceptable diluent. Examples include solid carriers such as talc, bentonite, clay, kaolin, diatomaceous earth, white carbon, vermiculite, slaked lime, ammonium sulfate and urea; liquid carriers such as water, alcohols, dioxane, acetone, xylene, cyclohexane, methylnaphthalene, dimethylformamide, N-methylpyrrolidone, dimethyl sulfoxide, cyclohexanone, methyl ethyl ketone and methyl isobutyl ketone; surface-active agents, emulsifiers or dispersants such as alkylsulfuric acid esters, alkylsulfonic acid salts, ligninsulfonic acid salts, polyoxyethylene glycol ethers, polyoxyethylene alkylaryl ethers, polyoxyethylene sorbitan monoalkylates and dinaphthylmethanedisulfonic acid salts; and various adjuvants such as carboxylmethyl cellulose and gum arabic.

For example, such a formulation can be prepared by mixing the compound of this invention with the aforesaid carrier and/or emulsifier, etc.

The compound of this invention may be present is a proportion of usually 0.01 to 99% by weight, preferably 0.1 to 95% by weight, in the formulation.

The compound of this invention, as such or in admixture with another active compound or as the aforesaid formulation, can be applied to plants by usual methods such as spraying, atomizing, or dusting.

The following examples illustrate the present invention in greater detail.

In these examples, all parts are by weight unless otherwise specified. The herbicidal activity of the active test compounds was evaluated on a scale of 0 to 5 in which 0 means that the plants were as sound as before the application of the active compound and 5 means that the application of the active compound caused the plants to wither and die, and 1, 2, 3 and 4 mean varying degrees of damaged state of the plants between 0 and 5.

EXAMPLE 1

Synthesis of compound (100):

A mixture of 10.3 parts of glycine ethyl ester, 10.6 parts of triethylamine and 200 parts of diethyl ether was stirred with ice cooling, and a solution of 15.8 parts of bromoacetyl chloride in 100 parts of diethyl ether was added dropwise. After the addition, the temperature of the mixture was returned to room temperature, and the reaction mixture was washed with water. The oil layer was separated and evaporated to dryness. To the residue were added 27.3 parts of 4-(6-chloro-quinoxalyl-2-oxy)phenol, 27.6 parts of anhydrous potassium carbonate and 300 parts of methyl ethyl ketone, and the mixture was heated under reflux for 2 hours. The reaction mixture was washed with water. The organic layer was separated, and concentrated to dryness under reduced pressure to give 35 parts of the desired compound. The IR and NMR spectral data of this compound are shown in Table 1.

EXAMPLES 2-14

The compounds indicated in Table 1 were obtained by repeating Example 1 except that the compounds of the following formula

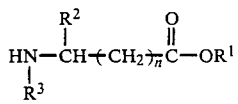

were used instead of glycine ethyl ester [in the above formula, $R^1$, $R^2$ and $R^3$ are the same as in general formula (I)].

TABLE 1

Structure:

$$X\text{-benzo[pyrazine]-O-C}_6H_4\text{-OCH}_2\text{CN(R}^3)\text{-CH(R}^2)\text{-(CH}_2)_n\text{-C(O)-OR}^1$$

| Example | Compound No. | X | $R^1$ | $R^2$ | $R^3$ | n | IR $\nu$(cm$^{-1}$) | NMR solv | $\delta$(ppm) | |
|---------|--------------|----|-------|-------|-------|---|---------------------|----------|----|----|
| 1 | 100 | Cl | $C_2H_5$ | H | H | 0 | 3300, 1740, 1660, 1600 | CDCl$_3$ | 1.30, 4.15, 4.26, 4.60, 6.8–7.4, 7.63, 8.05, 8.65 | (3H), (2H), (2H), (2H), (5H), (2H), (1H), (1H) |
| 2 | 132 | Cl | $-^nC_4H_9$ | H | H | 0 | 3300, 1740, 1660, 1600 | CDCl$_3$ | 0.93, 1.0–2.0, 4.10, 4.15, 4.53, 6.9–7.5, 7.63, 8.05, 8.65 | (3H), (4H), (2H), (2H), (2H), (5H), (2H), (1H), (1H) |
| 3 | 102 | Cl | $CH_3$ | $CH_3$ | H | 0 | 3280, 1740, 1660, 1600 | CDCl$_3$ | 1.50, 3.80, 4.60, 4.80, 6.8–7.5, 7.60, 8.00, 8.60 | (3H), (3H), (2H), (1H), (5H), (2H), (1H), (1H) |
| 4 | 104 | Cl | $CH_3$ | $-CH_2-C_6H_5$ | H | 0 | 3300, 1740, 1660, 1600 | CDCl$_3$ | 3.16, 3.75, 4.55, 4.7–5.2, 6.7–7.5, 7.60, 8.00, 8.65 | (2H), (3H), (2H), (1H), (10H), (2H), (1H), (1H) |
| 5 | 106 | Cl | $CH_3$ | $-C_6H_5$ | H | 0 | 3270, 1745, 1640, 1600 | CDCl$_3$ | 3.75, 4.55, 5.70, 6.8–7.5, 7.60, 8.05, 8.65 | (3H), (2H), (1H), (10H), (2H), (1H), (1H) |
| 6 | 108 | Cl | $-^nC_4H_9$ | $-C_6H_5$ | H | 0 | 3400, 3300, 1740, 1670, 1600 | CDCl$_3$ | 0.85, 0.9–2.0, 4.15, 4.55, 5.65, 6.9–7.5, 7.60, 8.00, 8.65 | (3H), (4H), (2H), (2H), (1H), (10H), (2H), (1H), (1H) |
| 7 | 110 | Cl | $CH_3$ | $-CH_2COOCH_3$ | H | 0 | 3400, 3300, 1730, 1660, 1600 | CDCl$_3$ | 3.00, 3.70, 3.77, 4.60, 5.00, 6.9–7.5, 7.60 | (2H), (3H), (3H), (2H), (1H), (5H), (2H) |

TABLE 1-continued

| Example | Compound No. | X | R¹ | R² | R³ | n | IR ν(cm⁻¹) | solv | NMR δ(ppm) | |
|---------|--------------|---|----|----|----|---|------------|------|---|---|
| | | | | | | | | | 8.00 | (1H) |
| | | | | | | | | | 8.65 | (1H) |
| 8 | 112 | Cl | CH₃ | —CH₂CHCH₃<br>            \|<br>           CH₃ | H | 0 | 3300<br>1740<br>1660<br>1600 | CDCl₃ | 0.95<br>1.5–1.9<br>3.75<br>4.60<br>4.80<br>6.9–7.5<br>7.60<br>8.00<br>8.65 | (6H)<br>(3H)<br>(3H)<br>(2H)<br>(1H)<br>(5H)<br>(2H)<br>(1H)<br>(1H) |
| 9 | 114 | Cl | CH₃ | C₂H₅ | H | 0 | 3300<br>1740<br>1660<br>1600 | CDCl₃ | 0.9<br>1.6–2.1<br>3.75<br>4.60<br>4.80<br>6.9–7.5<br>7.60<br>8.00<br>8.65 | (3H)<br>(2H)<br>(3H)<br>(2H)<br>(1H)<br>(5H)<br>(2H)<br>(1H)<br>(1H) |
| 10 | 116 | Cl | CH₃ | H | CH₃ | 0 | 1750<br>1665<br>1595 | CDCl₃ | 3.20<br>3.75<br>4.20<br>4.83<br>6.9–7.5<br>7.60<br>8.00<br>8.65 | (3H)<br>(3H)<br>(2H)<br>(2H)<br>(4H)<br>(2H)<br>(1H)<br>(1H) |
| 11 | 118 | Cl | H | 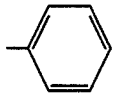 | H | 0 | 3400<br>1720<br>1660<br>1570 | DMSO-d₆ | 4.70<br>5.10<br>7.0–7.6<br>7.70<br>8.10<br>8.3–8.6<br>8.70 | (2H)<br>(1H)<br>(10H)<br>(2H)<br>(1H)<br>(1H)<br>(1H) |
| 12 | 124 | Cl | CH₃ | H | H | 1 | 3300<br>1740<br>1660<br>1600 | CDCl₃ | 2.65<br>3.70<br>3.75<br>4.55<br>6.9–7.5<br>7.60<br>8.00<br>8.65 | (2H)<br>(2H)<br>(3H)<br>(2H)<br>(5H)<br>(2H)<br>(1H)<br>(1H) |
| 13 | 126 | Cl | CH₃ | H | H | 2 | 3280<br>1740<br>1660<br>1600 | CDCl₃ | 1.93<br>2.36<br>3.40<br>3.70<br>4.53<br>6.9–7.5<br>7.60<br>8.00<br>8.60 | (2H)<br>(2H)<br>(2H)<br>(3H)<br>(2H)<br>(5H)<br>(2H)<br>(1H)<br>(1H) |
| 14 | 128 | Cl | CH₃ | —CH₂—CH₂—CH₂— | | 0 | 1740<br>1645<br>1600 | CDCl₃ | 1.7–2.4<br>3.75<br>3.6–3.8<br>4.55<br>4.65<br>6.9–7.5<br>7.60<br>8.00<br>8.60 | (4H)<br>(3H)<br>(2H)<br>(2H)<br>(1H)<br>(5H)<br>(2H)<br>(1H)<br>(1H) |

TABLE 1-continued

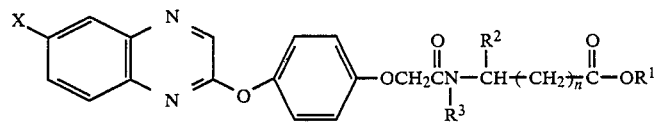

| Example | Compound No. | Compound X | R¹ | R² | R³ | n | IR $\nu$(cm$^{-1}$) | NMR solv | $\delta$(ppm) | |
|---|---|---|---|---|---|---|---|---|---|---|
| 15 | 130 | Cl | CH₃ | —CH₂CH₂—SCH₃ | H | 0 | 3300<br>1735<br>1660<br>1600 | CDCl₃ | 1.9–2.5<br>2.10<br>3.75<br>4.55<br>4.75<br>6.9–7.5<br>7.60<br>8.00<br>8.65 | (4H)<br>(3H)<br>(3H)<br>(2H)<br>(1H)<br>(5H)<br>(2H)<br>(1H)<br>(1H) |

EXAMPLE 16

Compound 5 (4.8 parts) obtained in Example 5 was added to 20 parts of a mixture of water and methanol (1:1 by volume), and 20 parts of a 1N aqueous solution of potassium hydroxide was added. The mixture was stirred at room temperature for 2 hours. The pH of the reaction mixture was adjusted to 3 with dilute hydrochloric acid, and the reaction mixture was extracted with diethyl ether. The etheric layer was dried over anhydrous sodium sulfate, and the ether was distilled off under reduced pressure to give 4.2 parts of carboxylic acid.

EXAMPLES 17–18

The carboxylic acid obtained in Example 16 was suspended in water, and an equimolar proportion of an aqueous solution of sodium hydroxide was added to form a uniform solution. Under reduced pressure, water was evaporated to dryness to obtain a sodium salt of the carboxylic acid. By using various bases instead of the aqueous solution of sodium hydroxide, the corresponding salts were obtained. The spectral data of these compounds are shown in Table 2.

FORMULATION EXAMPLE

One part of an active compound in accordance with this invention was added to 5000 parts of a mixture of acetone and water (1:1 by volume), and 2.6 parts of a nonionic surfactant (Sorpol 2680, tradename) to form a solution.

EXAMPLE 19

Active compounds in accordance with this invention were formulated in accordance with Formulation Example above.

Test plants were those obtained by sowing seeds in soil and growing them for 2 to 3 weeks after emergence.

The formulations containing the active compounds of this invention were applied in predetermined dosages, and thereafter, the plants were grown for 3 weeks without applying the formulations. The results are shown in Table 3.

COMPARATIVE EXAMPLE 1

Ethyl 2-[4-(6-chloro-2-quinoxalyloxy)phenoxy]propionate (compound A) was formulated in accordance with Formulation Example. The formulation was applied to plants in the same way as in Example 19, and the plants were observed. The results are also shown in Table 3.

TABLE 2

| Example | Compound No. | X | A⊕ | R² | R³ | n | IR $\nu$(cm$^{-1}$) |
|---|---|---|---|---|---|---|---|
| 17 | 120 | Cl | H₃⊕NC₂H₅ | –C₆H₅(benzyl) | H | 0 | 3400<br>2100<br>1660<br>1580 |
| 18 | 122 | Cl | Na⊕ | –C₆H₅(benzyl) | H | 0 | 3400<br>1660<br>1530 |

TABLE 3

| Compound No. | Rate of application (g/10 a) | Plant A | B | C | D | E | F | G | H | I | J |
|---|---|---|---|---|---|---|---|---|---|---|---|
| 100 | 50 | 5 | 4 | 5 | 5 | 5 | 5 | 5 | 0 | 0 | 0 |
| 132 | 100 | 5 | 5 | 5 | 4 | 4 | 4 | 4 | 0 | 0 | 0 |
| 102 | 50 | 5 | 4 | 4 | 5 | 4 | 4 | 4 | 2 | 2 | 0 |

TABLE 3-continued

| Compound No. | Rate of application (g/10 a) | Plant |   |   |   |   |   |   |   |   |   |
|---|---|---|---|---|---|---|---|---|---|---|---|
|   |   | A | B | C | D | E | F | G | H | I | J |
| 104 | 50  | 5 | 4 | 4 | 5 | 4 | 2 | 4 | 0 | 0 | 0 |
| 106 | 100 | 5 | 4 | 4 | 4 | 4 | 2 | 4 | 0 | 0 | 0 |
| 108 | 100 | 5 | 4 | 4 | 4 | 4 | 2 | 4 | 0 | 0 | 0 |
| 110 | 100 | 5 | 4 | 4 | 5 | 5 | 5 | 5 | 0 | 5 | 0 |
| 112 | 50  | 5 | 3 | 4 | 5 | 5 | 4 | 5 | 0 | 0 | 0 |
| 114 | 50  | 5 | 4 | 4 | 5 | 5 | 4 | 5 | 0 | 0 | 0 |
| 116 | 100 | 5 | 4 | 4 | 5 | 5 | 2 | 5 | 0 | 0 | 0 |
| 118 | 100 | 5 | 4 | 4 | 4 | 4 | 2 | 4 | 0 | 0 | 0 |
| 120 | 100 | 5 | 1 | 2 | 5 | 5 | 0 | 5 | 0 | 0 | 0 |
| 122 | 100 | 5 | 1 | 2 | 5 | 5 | 0 | 5 | 0 | 0 | 0 |
| 124 | 100 | 5 | 5 | 5 | 5 | 4 | 3 | 5 | 1 | 5 | 0 |
| 126 | 100 | 5 | 4 | 4 | 5 | 4 | 2 | 4 | 0 | 0 | 0 |
| A   | 100 | 5 | 5 | 5 | 5 | 5 | 5 | 5 | 5 | 5 | 1 |

The letters given in the column of "Plant" in Table 3 and other tables indicate the following plants.
A: *Digitaria adscendens*
B: *Setaria viridis*
C: *Setaria faberi*
D: *Echinochloa crus-galli*
E: *Poa annua*
F: *Sorghum halepense*
G: *Panicum texanum*
H: rice
I: corn
J: soybean

EXAMPLE 20

Seeds of plants were sown in soil, and on the second day after sowing, treated as follows. The growth of the plants was then observed for 3 weeks.

The formulations prepared as above were applied to the surface of the soil after sowing in predetermined dosages, and then the plants were grown for 3 weeks without applying the formulations. The results are shown in Table 4.

TABLE 4

| Compound No. | Rate of application (g/10 a) | Plant |   |   |   |   |
|---|---|---|---|---|---|---|
|   |   | A | B | F | I | J |
| 102 | 100 | 5 | 3 | 5 | 1 | 0 |
| 106 | 100 | 5 | 4 | 5 | 0 | 0 |
| 114 | 100 | 5 | 5 | 5 | 0 | 0 |
| 122 | 100 | 5 | 5 | 5 | 0 | 0 |

EXAMPLES 21-26

The compounds shown in Table 5 were obtained by repeating Example 1 except that a predetermined amount of a compound of formula

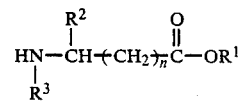

was used instead of glycine ethyl ester, and a predetermined amount of 2-bromopropionyl chloride was used instead of bromoacetyl chloride [in which $R^1$, $R^3$ and $R^5$ are as defined in general formula (II) above]. The IR and NMR spectral data of these compounds are shown in Table 5.

The carboxylic acid obtained in Example 27 was treated with bases in the same way as in Examples 17 and 18 to give its salts. The IR spectral data of the salts are shown in Table 6.

TABLE 5

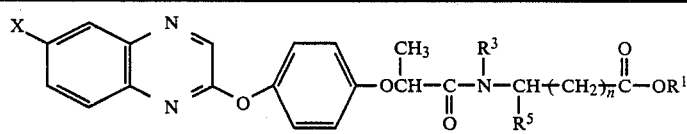

| Example | Compound No. | X | $R^1$ | $R^5$ | $R^3$ | n | IR $\nu(cm^{-1})$ | NMR solv. | $\delta$(ppm) |   |
|---|---|---|---|---|---|---|---|---|---|---|
| 21 | 200 | Cl | —CH$_3$ | —C$_6$H$_5$ | H | 0 | 3320<br>1740<br>1665<br>1600 | CDCl$_3$ | 1.60<br>3.73<br>4.73<br>5.60<br>6.7–7.8<br>8.05<br>8.65 | (3H)<br>(3H)<br>(1H)<br>(1H)<br>(12H)<br>(1H)<br>(1H) |
| 22 | 210 | Cl | —CH$_3$ | —CH$_2$CO$_2$CH$_3$ | H | 0 | 3350<br>1730<br>1660<br>1600 | CDCl$_3$ | 1.65<br>2.95<br>3.70<br>3.80<br>4.2–4.8<br>6.8–7.4<br>7.60<br>8.05<br>8.65 | (3H)<br>(2H)<br>(3H)<br>(3H)<br>(2H)<br>(5H)<br>(2H)<br>(1H)<br>(1H) |
| 23 | 212 | Cl | —CH$_3$ | ⁺(CH$_2$)$_2$SCH$_3$ | H | 0 | 3300<br>1735<br>1660<br>1600 | CDCl$_3$ | 1.60<br>1.9–2.5<br>2.10<br>3.70<br>4.2–4.8<br>6.8–7.4<br>7.60<br>8.05<br>8.65 | (3H)<br>(4H)<br>(3H)<br>(3H)<br>(2H)<br>(5H)<br>(2H)<br>(1H)<br>(1H) |

TABLE 5-continued

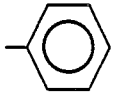

| Example | Compound No. | X | R¹ | R⁵ | R³ | n | IR ν(cm⁻¹) | NMR solv. | δ(ppm) | |
|---|---|---|---|---|---|---|---|---|---|---|
| 24 | 202 | Cl | H | ⟨phenyl⟩ | H | 0 | 3400<br>1720<br>1660<br>1570 | DMSO-d₆ | 1.65<br>4.80<br>5.15<br>7.0–7.6<br>8.10<br>8.3–8.6<br>8.70 | (3H)<br>(1H)<br>(1H)<br>(12H)<br>(1H)<br>(1H)<br>(1H) |

TABLE 6

| Example | Compound No. | X | A⊕ | R⁵ | R³ | n | IR ν(cm⁻¹) |
|---|---|---|---|---|---|---|---|
| 25 | 204 | Cl | H₃⊕NC₂H₅ | ⟨phenyl⟩ | H | 0 | 3400<br>2105<br>1660<br>1580 |
| 26 | 206 | Cl | Na⊕ | ⟨phenyl⟩ | H | 0 | 3400<br>1660<br>1530 |

EXAMPLE 27

The compounds obtained in Examples 21 to 26 were formulated in accordance with Formulation Example. The formulations were applied to plants in the same way as in Example 19, and the plants were observed. The results are shown in Table 7.

TABLE 7

| Compound No. | Rate of application (g/10 a) | A | B | C | D | E | F | G | H | I | J |
|---|---|---|---|---|---|---|---|---|---|---|---|
| 200 | 100 | 5 | 5 | 4 | 5 | 5 | 5 | 0 | 2 | 5 | 0 |
| 202 | 100 | 5 | 5 | | | | 5 | | | 5 | 0 |
| 204 | 100 | 5 | 5 | | | | 5 | | | 5 | 0 |
| 206 | 100 | 5 | 5 | | | | 5 | | | 5 | 0 |
| 210 | 100 | 5 | | | | | | | 2 | 5 | 0 |
| 212 | 100 | 5 | | | | | | | 2 | 5 | 0 |

EXAMPLE 28

The compound obtained in Example 21 was formulated in accordance with Formulation Example, and applied to the surface of the soil in the same way as in Example 19. The plants were then observed as in Example 19. The results are shown in Table 8.

TABLE 8

| Compound No. | Rate of application (g/10 a) | A | B | F | I | J |
|---|---|---|---|---|---|---|
| 200 | 100 | 5 | 5 | 4 | 5 | 0 |

What is claimed is:

1. A phenoxyacetic acid represented by the following formula (I)

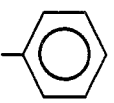

wherein X represents a halogen atom, R¹ and R³ are identical or different and each represents a hydrogen atom or an alkyl group having not more than 5 carbon atoms, R² represents a hydrogen atom, a lower alkyl group, a phenyl group, a benzyl group, —CH₂CH₂SCH₃, —CH₂OH, —CH(CH₃)OH, —CH₂SH, —CH₂COOCH₃,

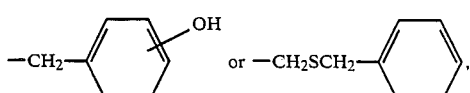

or $R^2$ and $R^3$ together may form —$CH_2CH_2CH_2$— or —$CH_2CH_2CH(OH)$—, and n is 0, 1 or 2, or a salt at the carboxyl group of the phenoxyacetic acid of the above formula in which $R^1$ is a hydrogen atom.

2. The compound of claim 1 wherein X in formula (I) is a halogen atom.

3. The compound of claim 1 wherein X in formula (I) is a chlorine atom.

4. A phenoxyacetic acid of claim 1 represented by the following formula (I)-a

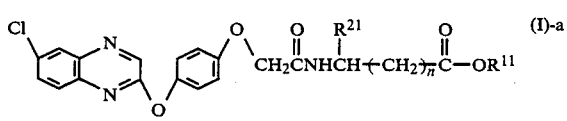
(I)-a wherein $R^{11}$ represents a hydrogen atom or an alkyl group having not more than 4 carbon atoms, $R^{21}$ represents a hydrogen atom, an alkyl group having not more than 4 carbon atoms, a phenyl group or a benzyl group, and n is as defined in claim 1, or a salt at the carboxyl group of the phenoxyacetic acid or the above formula in which $R^{11}$ is a hydrogen atom.

5. A method of eradicating weeds, which comprises applying a phenoxyacetic acid of formula (I) or its salt according to claim 1 to a locus where a narrow-leaved weeds are growing or are likely to grow, in an amount effective for eradicating the weeds.

6. A phenoxyacetic acid of claim 1 represented by the following formula (I)-b

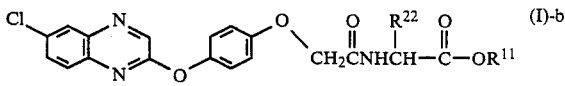
(I)-b wherein $R^{11}$ represents a hydrogen atom or an alkyl group having not more than 4 carbon atoms, and $R^{22}$ represents a phenyl or benzyl group, or a salt at the carboxyl group of the phenoxyacetic acid of the above formula in which $R^{11}$ is a hydrogen atom.

7. A herbicidal composition comprising a phenoxyacetic acid of formula (I) or its salt according to claim 1 as a herbicidally active ingredient, and a carrier therefor.

8. A herbicidal composition comprising a phenoxyacetic acid of formula (I)-a or its salt according to claim 4 as a herbicidally active ingredient, and a carrier therefor.

9. A herbicidal composition comprising a phenoxyacetic acid of formula (I)-b or its salt according to claim 6 as a herbicidally active ingredient, and a carrier therefor.

10. A method of eradicating weeds, which comprises applying a phenoxyacetic acid of formula (I)-a or its salt according to claim 4 to a locus where a broad-leaved crop is cultivated and where narrow-leaved weeds are growing or are likely to grow, in an amount effective for eradicating the weeds.

11. A method of eradicating weeds, which comprises applying a phenoxyacetic acid of formula (I)-b or its salt according to claim 6 to a locus where a narrow-leaved crop is cultivated and where narrow-leaved weeds are growing or are likely to grow, in an amount effective for eradicating the weeds.

* * * * *